(12) United States Patent
Schwarz et al.

(10) Patent No.: US 9,498,563 B2
(45) Date of Patent: *Nov. 22, 2016

(54) MEDICAL ARTICLES HAVING THERAPEUTIC-AGENT-CONTAINING REGIONS FORMED FROM COALESCED POLYMER PARTICLES

(75) Inventors: Marlene C. Schwarz, Auburndale, MA (US); Robert E. Richard, Wrentham, MA (US); Sheng-Ping Zhong, Shrewsbury, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1131 days.

This patent is subject to a terminal disclaimer.

(21) Appl. No.: 10/830,950

(22) Filed: Apr. 23, 2004

(65) Prior Publication Data

US 2005/0239508 A1   Oct. 27, 2005

(51) Int. Cl.
| | |
|---|---|
| *A61F 2/82* | (2013.01) |
| *A61L 29/16* | (2006.01) |
| *A61L 27/34* | (2006.01) |
| *A61L 27/54* | (2006.01) |
| *A61L 29/08* | (2006.01) |
| *A61L 31/10* | (2006.01) |
| *A61L 31/16* | (2006.01) |

(52) U.S. Cl.
CPC ............... *A61L 29/16* (2013.01); *A61L 27/34* (2013.01); *A61L 27/54* (2013.01); *A61L 29/085* (2013.01); *A61L 31/10* (2013.01); *A61L 31/16* (2013.01); *A61F 2250/0067* (2013.01); *A61L 2300/606* (2013.01)

(58) Field of Classification Search
USPC ............... 623/1.39–1.48; 427/2.24, 2.25
See application file for complete search history.

(56) References Cited

U.S. PATENT DOCUMENTS

| | | | |
|---|---|---|---|
| 4,177,177 A | 12/1979 | Vanderhoff et al. | 260/29.2 |
| 4,946,899 A | 8/1990 | Kennedy et al. | 525/244 |
| 5,025,004 A | 6/1991 | Wu et al. | 514/165 |
| 5,089,205 A | 2/1992 | Huang et al. | 264/255 |

(Continued)

FOREIGN PATENT DOCUMENTS

| | | | |
|---|---|---|---|
| WO | WO 03/028783 A1 | 4/2003 | A61L 29/12 |
| WO | 03080147 A1 | 10/2003 | |

OTHER PUBLICATIONS

Sastry et al., "Aqueous-based polymeric dispersion: preparation and characterization of cellulose acetate pseudolatex", International Journal of Pharmaceutics 165, pp. 175-189. 1998.

(Continued)

*Primary Examiner* — Thomas J Sweet
*Assistant Examiner* — Cheryl Miller
(74) *Attorney, Agent, or Firm* — Seager, Tufte & Wickhem, LLP

(57) ABSTRACT

Medical articles, such as drug-releasing patches or implantable or insertable medical devices, which are made up of a medical article substrate and a therapeutic-agent-containing region. The therapeutic-agent-containing region is made up of (i) a water-dispersible therapeutic agent and (ii) coalesced polymer particles supplied by an aqueous dispersion. Also described are methods of forming such medical articles, and methods of releasing a therapeutic agent within a patient using such medical articles.

5 Claims, 1 Drawing Sheet

(56) References Cited

U.S. PATENT DOCUMENTS

| | | | |
|---|---|---|---|
| 5,258,020 A | 11/1993 | Froix | 623/1 |
| 5,304,121 A | 4/1994 | Sahatjian | 604/53 |
| 5,500,161 A | 3/1996 | Andrianov et al. | 265/8 |
| 5,550,179 A | 8/1996 | Srourian | 524/210 |
| 5,616,608 A | 4/1997 | Kinsella et al. | 514/449 |
| 5,716,981 A | 2/1998 | Hunter et al. | 514/449 |
| 5,720,943 A | 2/1998 | Mougin et al. | 424/61 |
| 5,733,925 A | 3/1998 | Kunz et al. | 514/449 |
| 5,741,331 A | 4/1998 | Pinchuk | 623/11 |
| 5,879,697 A | 3/1999 | Ding et al. | 424/422 |
| 5,919,408 A | 7/1999 | Muller et al. | 264/5 |
| 5,954,706 A | 9/1999 | Sahatjian | 604/509 |
| 6,005,020 A | 12/1999 | Loomis | 523/105 |
| 6,099,652 A | 8/2000 | Patten, Jr. et al. | 118/724 |
| 6,110,483 A | 8/2000 | Whitbourne et al. | 424/423 |
| 6,110,998 A | 8/2000 | Slinkard et al. | 524/108 |
| 6,179,817 B1 | 1/2001 | Zhong | 604/265 |
| 6,280,411 B1 | 8/2001 | Lennox | 604/103.05 |
| 6,290,722 B1* | 9/2001 | Wang | 623/1.46 |
| 6,306,419 B1* | 10/2001 | Vachon | A61K 9/7023 424/422 |
| 6,335,029 B1 | 1/2002 | Kamath et al. | 424/423 |
| 6,368,658 B1* | 4/2002 | Schwarz et al. | 427/2.15 |
| 6,545,097 B2* | 4/2003 | Pinchuk et al. | 525/240 |
| 6,730,064 B2* | 5/2004 | Ragheb et al. | 604/265 |
| 6,780,930 B2* | 8/2004 | Lewis | C08F 246/00 524/800 |
| 6,805,898 B1* | 10/2004 | Wu et al. | 427/2.25 |
| 6,979,348 B2* | 12/2005 | Sundar | 623/1.15 |
| 7,285,304 B1* | 10/2007 | Hossainy et al. | 427/2.24 |
| 7,501,179 B2* | 3/2009 | Song | A61K 9/1635 428/402 |
| 7,537,781 B2* | 5/2009 | Richard | 424/425 |
| 2001/0021739 A1 | 9/2001 | Thames et al. | 524/400 |
| 2001/0027237 A1 | 10/2001 | Mayes et al. | 525/326.1 |
| 2002/0086808 A1* | 7/2002 | Nyssen | A01N 25/04 510/417 |
| 2002/0111590 A1 | 8/2002 | Davila et al. | 604/265 |
| 2003/0008990 A1 | 1/2003 | McCarthy | 526/247 |
| 2003/0060381 A1 | 3/2003 | Meier et al. | 510/141 |
| 2003/0118649 A1* | 6/2003 | Gao et al. | 424/471 |
| 2003/0139795 A1* | 7/2003 | Olson | A61F 2/95 623/1.11 |
| 2003/0143315 A1* | 7/2003 | Pui | A61L 31/16 427/2.1 |
| 2003/0203000 A1* | 10/2003 | Schwarz et al. | 424/423 |
| 2003/0203991 A1* | 10/2003 | Schottman et al. | 523/334 |
| 2003/0235603 A1* | 12/2003 | Schwarz et al. | 424/426 |
| 2003/0236513 A1* | 12/2003 | Schwarz et al. | 604/890.1 |
| 2004/0106987 A1* | 6/2004 | Palasis et al. | 623/1.42 |
| 2004/0116551 A1* | 6/2004 | Terry | 523/122 |
| 2004/0142910 A1* | 7/2004 | Vachon | A61K 31/65 514/152 |
| 2005/0004306 A1* | 1/2005 | Lubnin et al. | 524/589 |
| 2005/0008671 A1* | 1/2005 | Van Antwerp | 424/423 |
| 2005/0025800 A1* | 2/2005 | Tan | 424/423 |
| 2005/0181014 A1* | 8/2005 | Richard | 424/426 |

OTHER PUBLICATIONS

Quintanar-Guerrero et al., "Pseudolatex preparation using a novel emulsion-diffusion process involving direct displacement of partially water-miscible solvents by distillation", International Journal of Pharmaceutics, 188 (2): 155-64, Oct. 25, 1999, 1 page abstract.
Robe, Gary; Mitchell, Jerry. "Making the Transition: Coalescing Aids for Latex Paints", Paint and Coatings Industry, http://www.pcimag.com/CDA/ArticleInformation/features/BNP_Features_Item/0,1846,00.html, pp. 1-8, date unknown but before filing date of this application.
http://www.metabolix.com/natures%20plastic/coalescing.html, "Coalescing Solvents", Metabolix, pp. 1-2, date unknown but before filed of this application.
Parrish, Dennis, "Emulsion Polymerization", http://www.psrc.usm.edu/macrog/emulsion.htm, pp. 1-4, copyright 1995,1996, Dept. of Polymer Science, University of Southern Mississippi.
Pearnchob, Nantharat, et al., "Dry Polymer Powder Coating and Comparison with Conventional Liquid-based coatings for Eudragit ® RS, Ethylcellulose and Shellac", *European Journal of Pharmaceutics and Biopharmaceutics*, vol. 56, No. 3 Nov. 2003, pp. 363-369.
S.A. Hagan et al., "Polylactide-Poly(ethylene glycol) Copolymers as Drug Delivery Systems. 1. Characterization of Water Dispersible Micelle-Forming Systems", Langmuir 1996, 12, pp. 2153-2161.

* cited by examiner

MEDICAL ARTICLES HAVING THERAPEUTIC-AGENT-CONTAINING REGIONS FORMED FROM COALESCED POLYMER PARTICLES

FIELD OF THE INVENTION

The present invention relates to medical articles, such as implantable or insertable medical devices, which comprise a therapeutic-agent-containing region for the controlled delivery of therapeutic agents.

BACKGROUND OF THE INVENTION

Medical articles are frequently used for delivery of one or more therapeutic agents to patients. For example, an implantable or insertable medical device, such as a stent or catheter, may be provided with a coating layer that contains a polymer and a therapeutic agent. Once the medical device is placed at a desired location within a patient, the therapeutic agent is released from the medical device into the patient, thereby achieving a desired therapeutic outcome.

In general, the formation of such coating layers is simplified where a solvent is available that can effectively dissolve both the therapeutic agent and the polymer of interest. In many instances, however, it is desirable to use water as a solvent, for example, where a preferred therapeutic agent is soluble in water or where solvent toxicity issues may arise. Unfortunately, many polymers that are desirable for the formation of therapeutic-agent-containing regions on medical articles (for example, biostable polymers) are insoluble in water, presenting difficulties in forming release regions. Present formulation techniques for such systems typically involve forming a solution of the polymer of choice in organic solvent and then attempting to disperse the drug in the solution. These techniques commonly require a substantial amount of mechanical agitation to keep the drug from settling out of solution, and can result in unacceptable phase separation in the final product.

SUMMARY OF THE INVENTION

The above and other challenges are addressed by the present invention. According to one aspect of the present invention, a medical article, for example, an implantable or insertable medical device, is provided, which comprises a medical article substrate and a therapeutic-agent-containing region disposed over the substrate. The therapeutic-agent-containing region further comprises (i) a therapeutic agent, for example, a water-dispersible therapeutic agent, and (ii) coalesced polymer particles, wherein the polymer particles are supplied from an aqueous dispersion. The therapeutic-agent-containing region is commonly a coating layer, which may be disposed over a fraction of the medical article substrate, or completely surround the medical article substrate.

Other aspects of the present invention concern methods of making medical articles, for example, implantable or insertable medical devices. These methods comprise: (a) providing a medical article substrate, (b) providing an aqueous dispersion comprising (i) polymer particles and (ii) a water-dispersible therapeutic agent, (c) contacting the medical article substrate with the aqueous dispersion (e.g., by spraying the aqueous dispersion on the substrate), and (d) forming a therapeutic-agent-containing region by removing the water from the dispersion (e.g., by evaporation) to coalesce the polymer particles.

Various methods are known for forming aqueous dispersions of polymer particles, including (a) emulsion polymerization processes, for example, those which comprise (i) forming an emulsion comprising surfactant, monomer, initiator and water, and (ii) polymerizing the monomer to produce the dispersion; (b) processes which comprise (i) forming an emulsion containing an aqueous phase, and an organic phase that comprises an organic solvent and polymer, and (ii) removing the organic solvent to produce the dispersion; and (c) processes in which hydrophilic groups are incorporated into otherwise hydrophobic polymers, among others.

Still other aspects of the present invention concern methods of releasing therapeutic agents within patients, which comprise providing medical articles like those above, and implanting or inserting the medical articles into a patient, for instance, into the vasculature of the patient for the treatment of restenosis.

The present invention is advantageous in that therapeutic-agent-containing regions can be provided on medical article substrates with relative ease, even in instances where a water-soluble therapeutic agent is provided in combination with a water-insoluble polymer.

Another advantage of the present invention is that a wide range of water-dispersible therapeutic agents can be screened for use by simply combining each therapeutic agent with an appropriate aqueous polymer dispersion, and applying the resulting dispersion to a medical article substrate, thereby minimizing process development efforts.

Another advantage of the present invention is that therapeutic-agent containing regions can be formed without subjecting the therapeutic agent to harsh processing conditions, for example, granulation processing to produce particulates for dispersion.

These and other embodiments and advantages of the present invention will become immediately apparent to those of ordinary skill in the art upon review of the Detailed Description and Claims to follow.

DETAILED DESCRIPTION OF THE INVENTION

Figure 1:
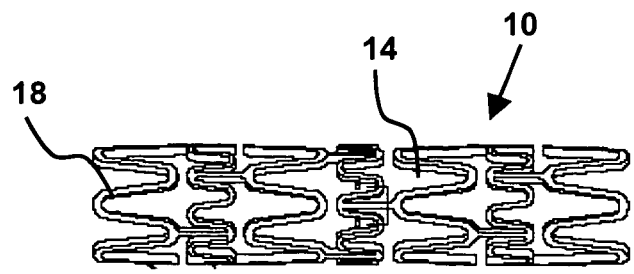
FIG. 1 is a schematic illustration of a stent in accordance with an embodiment of the invention.

According to one aspect of the present invention, a medical article is provided, which includes a medical article substrate and a therapeutic-agent-containing region disposed over the substrate. The therapeutic-agent-containing region comprises (i) a water-dispersible therapeutic agent and (ii) coalesced particles of an aqueous polymer dispersion, which particles contain one or more polymers.

The water-dispersible therapeutic agent can be a water-soluble therapeutic agent or a water-insoluble therapeutic agent that is nonetheless stable in aqueous solution, for example, a stable aqueous dispersion (including dispersions of liquid and solid therapeutic agents).

The therapeutic-agent-containing region may be disposed over the entirety of the medical article substrate or over only a portion of the medical article substrate. In many embodiments, the therapeutic-agent-containing region is in the form of a layer that extends over a least a portion of the medical article surface. As used herein a "layer" of a given material is a region of that material whose thickness is small compared to both its length and width (e.g., the length and width dimensions may both be at least 5, 10, 20, 50, 100 or more times the thickness dimension in some embodiments). As used herein a layer need not be planar, for example, taking on the contours of an underlying substrate. Layers can be discontinuous (e.g., patterned). "Film" and "layer" may be used interchangeably herein.

If desired, a barrier layer may be disposed between the therapeutic-agent-containing region and a site of intended release to further control the rate at which the therapeutic agent is released.

Medical articles of the present invention include any medical article for which controlled release of a therapeutic agent is desired. Examples of medical articles include patches for the delivery of therapeutic agent to intact skin, broken skin (including wounds) and surgical sites.

Examples of medical articles further include implantable or insertable medical devices, for instance, catheters (for example, renal or vascular catheters such as balloon catheters), guide wires, balloons, filters (e.g., vena cava filters), stents (including coronary vascular stents, cerebral, urethral, ureteral, biliary, tracheal, gastrointestinal and esophageal stents), stent grafts, cerebral aneurysm filler coils (including Guglilmi detachable coils and metal coils), vascular grafts, myocardial plugs, patches, pacemakers and pacemaker leads, heart valves, biopsy devices, or any coated substrate (which can comprise, for example, glass, metal, polymer, ceramic and combinations thereof) that is implanted or inserted into the body.

The medical articles of the present invention include drug delivery medical articles that are used for either systemic treatment or for the localized treatment of any mammalian tissue or organ. Non-limiting examples are tumors; organs including the heart, coronary and peripheral vascular system (referred to overall as "the vasculature"), lungs, trachea, esophagus, brain, liver, kidney, bladder, urethra and ureters, eye, intestines, stomach, pancreas, ovary, and prostate; skeletal muscle; smooth muscle; breast; cartilage; and bone. As used herein, "treatment" refers to the prevention of a disease or condition, the reduction or elimination of symptoms associated with a disease or condition or the substantial or complete elimination a disease or condition. Preferred subjects are mammalian subjects, more preferably human subjects.

Medical articles having sustained release profiles are beneficial in many cases. By "sustained release profile" is meant a release profile in which less than 25% of the total release from the medical article that occurs over the entire course of administration occurs after 1 day (or in some embodiments, after 2, 4, 8, 16, 32, 64, 128 or even more days) of administration. Conversely, this means that more than 75% of the total release that occurs from the medical article will occur after the device has been administered for the same period.

The release characteristics that are ultimately of interest are of course the release characteristics within the subject, for example, within a mammalian subject. However, it is well known in the art to test the release characteristics within an experimental system that gives a good indication of the actual release characteristics within the subject. For example, aqueous buffer systems such as Tris, phosphate buffered saline (e.g., PBS/0.5% Tween 20), and so forth are commonly used for testing release of therapeutic agents from vascular medical devices.

Specific examples of medical articles for use in conjunction with the present invention include vascular stents that are used to deliver therapeutic agent into the vasculature for the treatment of restenosis. In these embodiments, a therapeutic-agent-containing region in accordance with the present invention is typically provided over all or a portion of a stent substrate.

In this regard, FIG. 1 illustrates a vascular stent 10, in accordance with an embodiment of the present invention. Stent 10 can be, for example, a coronary stent, sized to fit in the blood vessel of a patient, which is formed from a plurality of structural elements 18. The construction of the stent 10 permits the stent 10 to be introduced into the vascular system in a collapsed configuration, minimizing the diameter of the stent 10. Stent 10 can then expand to an expanded position at the desired location within the blood vessel of the patient. The structural elements 18 of stent 10 form a frame, such as tubular shape, permitting the stent 10 to self-expand or to expand to the desired shape after an expansive force is applied, for example, by the expansion of a balloon within the stent. The structural elements 18 of stent 10 form windows 14 such that the stent 10 does not have a continuous outer shell. Windows 14 are generally present in most stent configurations, although the specific details of the shape of structural elements 18 and the construction of stent 10 can vary widely.

Figure 2:
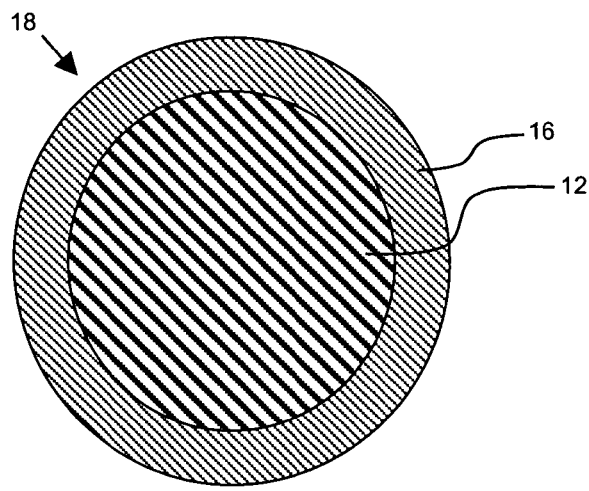
FIG. 2 is a schematic cross-sectional illustration of a structural element of a stent like that of FIG. 1, in accordance with an embodiment of the invention.

A therapeutic-agent-containing layer in accordance with the present invention is applied on the surface of each stent. For example, FIG. 2 is a schematic cross-sectional view of a structural element 18 like that of FIG. 1, in accordance with an embodiment of the invention. In FIG. 2, the therapeutic-agent-containing layer 16 is directly adjacent the underlying structural member 12, which acts as a substrate for the therapeutic-agent-containing layer 16.

Figure 3:
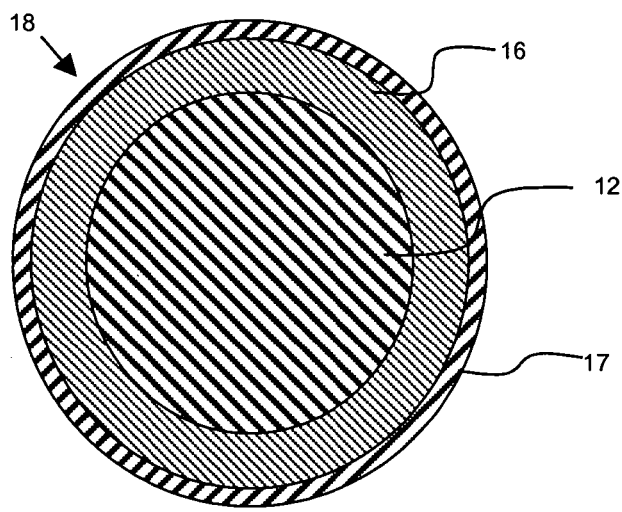
FIG. 3 is a schematic cross-sectional illustration of a structural element a stent like that of FIG. 1, in accordance with another embodiment of the invention.

FIG. 3 is also a schematic cross-sectional view of a structural element 18, in accordance with another embodiment of the invention. As in FIG. 2 above, the therapeutic-agent-containing layer 16 is directly adjacent the underlying structural member 12. In FIG. 3, however, an additional polymeric barrier layer 17 is provided over the therapeutic-agent-containing layer 16, for example, to delay delivery of therapeutic agent from the stent. Polymers for use as barrier layer materials can be selected from the various polymers listed elsewhere herein.

As noted above, the therapeutic-agent-containing regions of the medical articles of the present invention comprise (i) a therapeutic agent and (ii) coalesced polymer particles that originate from an aqueous dispersion. "Coalescence" is a process whereby polymer particles fuse (i.e., merge) together, for example, to form a layer.

Coalescence occurs independently of chemical reactions such as crosslinking reactions. Hence crosslinking agents need not be used in the practice of the present invention. In other embodiments, the therapeutic-agent-containing regions are crosslinked, for example, using covalent or ionic crosslinking agents, to further regulate therapeutic agent release.

By "aqueous dispersion" or "aqueous polymer dispersion" is meant a dispersion of polymer particles, which comprises water, typically 50% or more water. The dispersions can include further components besides polymer and water (e.g., surfactants, among numerous other components, several of which are described elsewhere herein). Various methods are known for producing the aqueous polymer dispersions for use in connection with the present invention.

Such aqueous polymer dispersions can be, for example, (a) prepared by emulsion polymerization or by building hydrophilic groups into the polymer structure as an internal emulsifier (hence, no external surfactant is required), in which case the resulting product is sometimes referred to as a "true latex", or (b) prepared from a previously formed polymer, in which case the resulting product is sometimes referred to as a "pseudolatex".

The polymer particles the aqueous dispersions are typically sufficiently small to enhance stability (e.g., sufficiently small such that the particles will not settle over the period of time needed to apply the dispersion to the medical article substrate, for instance, a period of hours, or even days or weeks in some cases). Small particles are also advantageous in that they tend to coalesce more readily than their larger counterparts. Hence, the aqueous dispersions that are used in connection with the present invention typically comprise particles with weight average diameters ranging from, for example, 0.001 to 10 microns, more typically from 0.01 to 1 micron.

Various emulsion polymerization processes are known for the formation of true latexes. In a typical emulsion polymerization process, surfactant (also sometimes referred to as an emulsion stabilizer), monomer, initiator (e.g., a free radical initiator) and water are combined, and the resulting mixture is emulsified to form an oil-in-water emulsion having monomer in the internal phase. Polymerization is then allowed to proceed, producing an aqueous dispersion of polymer particles.

Pseudolatexes (or "pseudolatices"), which are aqueous polymer dispersions prepared from previously formed polymers, can be formed using a number of techniques, including direct emulsification, emulsification by neutralization, inversion emulsification, and emulsification-diffusion polymerization, among others.

Direct emulsification is a process in which (a) an aqueous (i.e., water-containing) solution is admixed with (b) an organic solution that contains a water-insoluble polymer dissolved in one or more organic solvents. The organic solvent or solvents preferably have boiling points less than that of water. The resulting mixture is emulsified, forming droplets of the polymer solution, which are dispersed within the water phase. It may be necessary to stabilize the emulsion, in which case a surfactant such as an oil-in-water type emulsifier can be added. For example, (i) non-ionic surfactants such as a polyvinyl alcohol, polyvinylpyrrolidone, and polyoxyethylene/polyoxypropylene copolymer, (ii) anionic surfactants such as sodium lauryl sulfate, sodium dodecyl sulfate and disulfosuccinate and/or (iii) cationic surfactants such as benzalkonium chloride, dimethyl dioctodecyl ammonium bromide, dioleoyl-3-trimethylammonium-propane and cetyl trimethyl ammonium bromide, may be used. Very small particle sizes (e.g., on the order of a micron or less) can be achieved by subjecting the emulsion to high shear forces using, for example, rotor/stator technology (e.g., using Polytron® rotor/stator technology from Kinmatica Inc.), high pressure homogenization (e.g., using an APV-Gaulin microfluidizer or Gaulin homogenizer), mechanical shear (e.g., using a Gifford Wood colloid mill), or ultrasonification (e.g., using either a probe or a flow-through cell). Organic solvent is then selectively removed (e.g., by evaporation, by solvent distillation, or by another method of solvent removal) resulting in an aqueous dispersion of polymer particles.

Inversion emulsification is a process in which water is added to an organic solution of the polymer of interest, typically in the presence of an emulsifier (for example, an oil-in-water emulsifier which can function at least partially effectively as a water-in-oil emulsifier), so that a water-in-oil emulsion is initially formed. Upon further addition of water, the emulsion inverts to form an oil-in-water emulsion. As above, small particle sizes are typically achieved by subjecting the emulsion to very high shear forces, and the solvent is subsequently removed to form an aqueous polymer dispersion.

Emulsification-diffusion polymerization is a process in which partially water-miscible solvents are used. First, an organic solution of polymer (which is saturated with water) is emulsified in an aqueous solution of a stabilizing agent (which is saturated with solvent), followed by solvent removal (e.g., by solvent distillation). This technique relies on the rapid displacement of the solvent from the internal into the external phase, which thereby provokes polymer aggregation. Particle formation is believed to occur because rapid solvent diffusion produces regions of local supersaturation near the interface, and particles are formed due to the ensuing interfacial phase transformations and polymer aggregation that occur in these interfacial domains. Emulsification by neutralization is a process in which a polymer having functional acidic or basic groups is provided, and the polymer is ionized and emulsified in water by neutralizing these groups.

A variety of polymers can be used in connection with the aqueous polymer dispersions of the present invention. For example, the polymers may be homopolymers or copolymers (including alternating, random and block copolymers), cyclic, linear or branched (e.g., polymers have star, comb or dendritic architecture), natural or synthetic, thermoplastic or thermosetting. The polymers for use in connection with the present invention are commonly biostable polymers. A biostable polymer is one that maintains its structural integrity (i.e., it is substantially inert, in the presence of a physiological environment) for the time period during which the medical article is in contact (e.g., implanted or inserted) with the body.

Polymers for use in the practice of the invention can be selected from homopolymers, copolymers and blends of the following, among others: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS). polyvinyl ketones, polyvinylcarbazoles, and polyvinyl esters such as polyvinyl acetates; polybenzimidazoles; polyalkyl oxide polymers and copolymers including polyethylene oxides (PEO); polyesters including polyethylene terephthalates and aliphatic polyesters such as polymers and copolymers of lactide (which includes lactic acid as well as d-,1-and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyolefin polymers and copolymers, including polyalkylenes such as polypropylenes, polyethylenes (low and high density, low and high molecular weight), polybutylenes (such as polybut-1-ene and polyisobutylene), EPDM copolymers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid.

Examples include: (a) polyolefin polymers, for example, polyisobutylene, (b) polyolefin copolymers, for example, polyolefin-polyvinylaromatic copolymers such as polyisobutylene-polystyrene copolymers, poly(butadiene/butylene)-polystyrene copolymers, polyethylene/butylene-polystyrene copolymers and polybutadiene-polystyrene copolymers; (c) silicone polymers and copolymers; as well as (d) blends thereof. Specific examples of polyolefin-polyvinylaromatic copolymers include polyolefin-polyvinylaromatic diblock copolymers and polyvinylaromatic-polyolefin-polyvinylaromatic triblock copolymers, such as a polystyrene-poly(ethylene/butylenes)-polystyrene (SEBS) triblock copolymer, available as Kraton®, and polystyrene-polyisobutylene-polystyrene (SIBS) triblock copolymers, which are described, for example, in U.S. Pat. No. 5,741,331, U.S. Pat. No. 4,946,899 and U.S. Pat. No. 6,545,097, each of which is hereby incorporated by reference in its entirety. Additional polyolefin-polyvinylaromatic copolymers are set forth in the prior paragraph.

In some embodiments of the invention the polymer of choice is inherently dispersible or readily rendered dispersible (see, e.g., emulsification by neutralization above) in aqueous media. In other embodiments, the dispersibility in aqueous media of the polymer of choice is enhanced in any of a variety of ways, for example, by adding bulky steric groups or by adding charged groups or other water-soluble (i.e., hydrophilic) groups to the polymer, or otherwise to the dispersion.

For instance, various hydrophilic groups including charged groups (e.g., carboxylic acid groups and sulfonate groups) and polar groups (e.g., hydroxyl groups) can be built into a polymer structure to improve water dispersibility. Due to the hydrophilic characteristics of the resulting polymer, an aqueous dispersion can be readily formulated, frequently without the need for a surfactant, for example, if carboxylic acid groups or sulfonic acid groups are built into the polymer structure, those groups are neutralized by a quaternary amine such as diethanolamide (DEA). Then the polymer is added to water or other aqueous media under agitation to be dispersed. As noted above, it is beneficial in some instances to adjust the pH of the aqueous media to ionize acidic or basic groups.

In some embodiments, hydrophilic groups (e.g., charged groups, polar groups, etc.) are introduced into polymer structure via the polymerization of charged, ionizable, or otherwise hydrophilic monomers. In a specific embodiment, hydrophilic groups are polymerized into polystyrene-polyisobutylene block copolymer structures such as those discussed above to provide a water-dispersible polymer. Examples include introducing maleic anhydride monomers, sulfonate styrene monomers, acrylic acid monomers, hydroxyl-styrene monomers, or polyethylene oxide on modified styrene monomers, into the polystyrene-polyisobutylene block copolymer chain, either before, during or after polymerization of the polystyrene and polyisobutylene blocks.

In other embodiments, hydrophilic groups are introduced to a pre-existing polymer; for example, where a polystyrene-polyisobutylene block copolymer such as SIBS is sulfonated and neutralized to obtain a water-dispersible polymer.

In addition to preparation using the techniques such as those discussed above, aqueous polymer dispersions can also be obtained commercially. Examples of commercially available aqueous polymer dispersions include phenoxy resin dispersions, ethylene-acrylic acid (EAA) copolymer dispersions, acrylate-urethane copolymer dispersions, and polyurethane dispersions.

In some embodiments of the invention, an aqueous polymer dispersion is provided by combining two or more existing aqueous polymer dispersions. In this way, the resulting aqueous dispersion can contain distinct populations of polymer particles, which may differ, for example, in size, composition, and so forth.

The therapeutic-agent-containing regions of the present invention, which as noted above comprise therapeutic agent and coalesced polymer particles, can be formed using a variety of techniques. Typically, these techniques involve contacting a medical article substrate, or another template such as a mold or other release surface, with a therapeutic-agent-containing aqueous polymer dispersion, followed by a drying step.

Once an appropriate aqueous polymer dispersion is obtained, for example, by practicing one of the techniques discussed above or by obtaining a commercial preparation, it is a simple matter to incorporate one or more water-dispersible therapeutic agents (e.g., hydrophilic, water-soluble therapeutic agents or stable aqueous dispersions of water-insoluble therapeutic agents) into the same. For example, the therapeutic agent(s) can simply be added to the aqueous polymer dispersion with stirring to achieve a stable, uniform, therapeutic-agent-containing dispersion. The water-dispersible therapeutic agents are typically provided in the aqueous dispersions of interest at concentrations that yield therapeutically effective compositions upon removal of water and other volatile components from the dispersions.

One advantage of these characteristics of the invention is that a variety of therapeutic agents can be evaluated using the same aqueous polymer dispersion, with minimal formulation development work.

Preferred techniques for contacting a medical article substrate or other template with a therapeutic-agent-containing aqueous polymer dispersion include, casting techniques, spin coating techniques, web coating techniques, spraying techniques, dipping techniques, techniques involving coating via mechanical suspension including air suspension, ink jet techniques, electrostatic techniques, and combinations of these processes.

Where appropriate, the above application techniques can be repeated or combined with other application techniques to build up a layer to a desired thickness. The thickness of the layer can be varied in other ways as well. For example, in one process, spraying, coating thickness can be increased by modification of coating process parameters, including increasing spray flow rate, slowing the movement between the substrate to be coated and the spray nozzle, providing repeated passes and so forth.

In some beneficial embodiments of the invention, the aqueous polymer dispersion is provided with a cosolvent to facilitate the coating process. The cosolvent is typically miscible with water and a solvent for the therapeutic agent, while at the same time not being a solvent for the dispersed polymer.

During the drying step, water and any other volatile material such as a cosolvent are removed, and the polymer particles of the aqueous dispersion coalesce. Without wishing to be bound by theory, it is believed that, as the particles coalesce, the therapeutic agent becomes trapped between the particles as they fuse and is eventually dispersed throughout the dried film, resulting in a relatively uniform distribution of the therapeutic agent within the polymer film.

Where the aqueous dispersion comprises a polymer with hydrophobic and hydrophilic portions as previously discussed, the hydrophobic portions face inward to form a core, and the hydrophilic portions face outward to form a hydrophilic shell, thereby forming a stabilized particle. When the dispersion is subsequently dried, however, the dispersed particles undergo a phase reversal process (i.e., the hydrophilic portions of the polymer groups face inward and hydrophobic face outward) and the particles merge to become a continuous layer. Consequently, any water-dispersible drugs that are present will typically become distributed relatively uniformly within the polymer matrix.

The aqueous polymer dispersions used in connection with the present invention will commonly have a minimum film formation temperature ($T_{mff}$), which is the temperature below which the particles no longer coalesce. Accordingly, it may be desirable some instances to heat the applied polymer particles to a temperature above the $T_{mff}$ in order to fuse the particles. In other instances, it may be desirable to reduce the $T_{mff}$ of the aqueous polymer dispersion by adding a suitable coalescing agent to the same. A coalescing agent may be thought of as a partial solvent for the polymer particles. The action of the coalescing agent on the polymer particles allows them to coalesce into a continuous film at a temperature lower than would otherwise occur in the absence of the coalescing agent. Examples of some commonly used coalescing agents include ethylene glycol, diethylene glycol, propylene glycol, ethylene glycol monopropyl ether, ethylene glycol monobutyl ether, propylene glycol monobutyl ether, propylene glycol n-propyl ether, dipropylene glycol methyl ether, butoxyethanol, ethyl acetate, monobutyl ether ("butyl carbitol"), carbitol acetate, ethylene glycol monobutyl ether ("butyl cellusolve"), methyl cellusolve, isopropyl cellusolve, cellusolve acetate, n-butylacetate, diethylene glycol ethyl ether acetate, dipropylene glycol methyl ether acetate, 3-ethyl ethoxy propionate, propylene glycol ethyl ether acetate, 2,2,4-trimethyl-3-pentanediol monoisobutyrate and trimethyl monoisobutyrate.

To the extent that coalescence can be controlled, for example, by varying the temperature above and below the $T_{mff}$, it may be desirable to stop the process short of complete coalescence (and hence total incorporation of the therapeutic agent), to form some areas that are rich in drug and other areas that are rich in polymer. On a molecular scale, channels of drug may form within the coalesced polymer, along which the therapeutic agent can diffuse. Changes in morphology may also be achieved, for example, by changing the drying rate, the particle size, and so forth.

It is noted that various ionically charged dispersions, such those formed from neutralization of acrylic or sulfonate monomers, have improved adhesion to metal substrates upon drying, due to their ionic charge.

"Therapeutic agents", "pharmaceutically active agents", "pharmaceutically active materials", "drugs" and other related terms may be used interchangeably herein and include genetic therapeutic agents, non-genetic therapeutic agents and cells. Therapeutic agents may be used singly or in combination. The therapeutic agents for use in connection with the present invention can be selected from suitable members of the list of therapeutic agents to follow, among others.

Non-genetic therapeutic agents include: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) anti-neoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines and (r) hormones.

Specific examples of non-genetic therapeutic agents include Hfg (halofuginone), paclitaxel, sirolimus, everolimus, tacrolimus, cladribine, dexamethasone, estradiol, ABT-578 (Abbott Laboratories), trapidil, liprostin, Actinomcin D, Resten-NG, Ap-17, abciximab, clopidogrel and Ridogrel.

Genetic therapeutic agents include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., PCOR), cationic polymers (e.g., polyethyleneimine, polyethyleneimine (PE I)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells include cells of human origin (autologous or allogeneic), including whole bone marrow, bone marrow derived mono-nuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) ACE inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents are also disclosed in U.S. Pat. No. 5,733,925 assigned to NeoRx Corporation, the entire disclosure of which is incorporated by reference.

Some examples of preferred hydrophilic therapeutic agents include halofuginone hydrobromide, DNA, and salts of drugs having a free base form.

A wide range of therapeutic agent loadings can be used in connection with the medical articles of the present invention, with the amount of loading being readily determined by those of ordinary skill in the art and ultimately depending, for example, upon the condition to be treated, the nature of the therapeutic agent itself, the means by which the therapeutic agent is administered to the intended subject, and so forth.

EXAMPLES

Example 1

PKHW™ -35 resin (from Phenoxy Associates) is a PAPHEN™ phenoxy waterborne dispersion. Both carboxylic acid groups and hydroxyl groups are built into the polymer structure to form this dispersion. It has about 35% solid content with butoxyethanol (8-10%) as co-solvent and DMEA (1-3%) as neutralizing salt. Water-dispersible drugs can be readily blended into this dispersion to yield stable polymer/drug mixture.

Example 2

Primacor 59901 (from Dow Chemicals) is obtained as a resin, but can be readily dispersed in aqueous amine or other alkaline aqueous solution. Water-dispersible drugs can be mixed into this dispersion without phase separation. Upon drying, this carrier has excellent adhesion to metallic, cellulosic, glass and other substrates. The drugs are relatively uniformly distributed in the polymer matrix. Primacor 5980 (also from Dow Chemicals) is an ethylene-acrylic acid copolymer. The carboxylic acid acts as an internal emulsifier, allowing the copolymer to be dispersed in aqueous media. No surfactant is needed. Water-dispersible drugs can be added directly into this dispersion to obtain a uniform coating fluid. Many additional types of Primacor resins are available from Dow Chemicals.

Example 3

NeoPac E-130 (from NeoResins) is an aliphatic urethane/acrylate copolymer dispersion. The solid content is about 35%. Water-dispersible drugs can be readily added into this dispersion to form stable mixture. When applied to device surface, a strong polymer coating containing the drug(s) is obtained. The formulation has excellent adhesion to both metal and plastic substrates.

Example 4

Bayhydrol 110 (from Bayer AG) is an anionic dispersion of an aliphatic polyester urethane polymer in water. The solids content is about 35%. According to one embodiment, 8% (solid/solid) of a water-soluble drug such as halofuginone hydrobromide is added into this dispersion to achieve a stable mixture. The mixture is applied as coating on a stent. Upon drying, a strong polymer coating is obtained with halofuginone hydrobromide entrapped in the polymer matrix. The distribution of drug in the matrix is relatively uniform.

Example 5

NeoRez R-972 (from NeoResins) is an anionic dispersion of aliphatic polyurethane polymer in water. The solid content is about 39%. According to one embodiment, a water-soluble drug such as 5% heparin (solid/solid) is blended in to form a stable mixture. The mixture is applied to a medical device surface as coating. When dried, the heparin is entrapped in the polymer matrix in a relatively uniform distribution.

Example 6

Bayhydrol 123 (from Bayer AG) is an anionic dispersion of an aliphatic polycarbonate urethane polymer in water and n-methyl-1-2-pyrrolidone. The polycarbonate improves the biostability of the urethane after implantation. According to one embodiment, a water-soluble drug such as halofuginone hydrobromide is blended into this dispersion analogous to the above.

Although various embodiments are specifically illustrated and described herein, it will be appreciated that modifications and variations of the present invention are covered by the above teachings and are within the purview of the appended claims without departing from the spirit and intended scope of the invention.

The invention claimed is:
1. A medical article comprising:
a medical article substrate; and
a coating layer disposed over the medical article substrate;
wherein the coating layer comprises:
(i) a water-dispersible therapeutic agent that is not an antimicrobial agent; and
(ii) coalesced polymer particles of a block copolymer comprising a poly(alkylene) chain and a poly(vinyl aromatic) chain, the coalesced polymer particles formed by providing an aqueous dispersion of polymer particles having a weight average diameter ranging from 0.001 microns to 10 microns and coalescing the polymer particles to form the coalesced polymer particles, the block copolymer rendered dispersible in the aqueous dispersion via inclusion of charged hydrophilic groups;
wherein the medical article is configured to release the therapeutic agent once the medical article has been administered to a patient.
2. The medical article of claim 1, wherein the charged hydrophilic groups are selected from neutralized carboxylic acid groups and sulfonate groups.
3. The medical article of claim 1, wherein the coalesced polymer particles are formed from an aqueous dispersion of polymer particles having a weight average diameter ranging from 0.01 microns to 1 micron.
4. A medical article comprising:
a medical article substrate; and
a coating layer disposed over the medical article substrate;
wherein the coating layer comprises:

(i) a water-dispersible therapeutic agent that is not an antimicrobial agent; and (ii) coalesced polymer particles of a sulfonated polystyrene-polyisobutylene block copolymer that were coalesced from an aqueous dispersion of polystyrene-polyisobutylene polymer particles having a weight average diameter ranging from 0.001 microns to 10 microns;

wherein the medical article is configured to release the therapeutic agent once the medical article has been administered to a patient.

5. The medical article of claim 4, wherein the coalesced polymer particles are formed from an aqueous dispersion of polymer particles having a weight average diameter ranging from 0.01 microns to 1 micron.

* * * * *